United States Patent [19]

Patil et al.

[11] Patent Number: 4,959,390
[45] Date of Patent: Sep. 25, 1990

[54] POLYHYDROXYBENZYLOXY-PROPANOLAMINES

[75] Inventors: Ghanshyam Patil, Vernon Hills, Ill.; William L. Matier, Hockessin, Del.; Khuong H. X. Mai, Chatworth, Calif.

[73] Assignee: E. I. du Pont de Nemours and Company, Wilmington, Del.

[21] Appl. No.: 285,005

[22] Filed: Dec. 15, 1988

[51] Int. Cl.$^5$ .................. A61K 31/275; C07C 255/50
[52] U.S. Cl. ................................ 514/522; 514/629; 514/651; 544/59; 544/162; 544/390; 546/225; 546/226; 548/233; 548/235; 548/337; 548/341; 548/483; 548/492; 548/567; 549/69; 549/72; 549/480; 549/483; 558/218; 558/346
[58] Field of Search .............. 564/346, 218; 514/651, 514/522, 629; 558/422

[56] References Cited

U.S. PATENT DOCUMENTS 3,996,382  12/1976  Berntsson et al. .............. 514/651

FOREIGN PATENT DOCUMENTS 0037781  10/1981  European Pat. Off. ............ 564/346
0056533   6/1967  Fed. Rep. of Germany ...... 564/346

Primary Examiner—Glennon H. Hollrah
Assistant Examiner—Susan P. Treanor
Attorney, Agent, or Firm—Gildo E. Fato

[57] ABSTRACT

Compounds of the present invention, are represented by the general formula

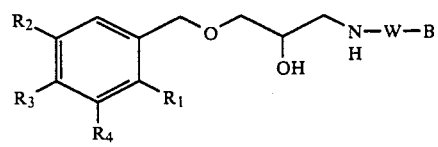

wherein $R_1$ group which may be alkyl of from 1 to about 6 carbon atoms, alkenyl of from 2 to about 6 carbon atoms, alkynyl of from 2 to about 10 carbon atoms, alkoxy wherein the alkyl group contains from 1 to about 6 carbon atoms, halogen, acetamido, amino, nitro, alkylamino of from 1 to about 6 carbon atoms, hydroxy, hydroxyalkyl of from 1 to about 6 carbon atoms, cyano or arylalkoxy wherein the alkyl group contains from 1 to about 6 carbon atoms $R_2$, $R_3$ and $R_4$ are hydrogen or hydroxyl groups or the combination of either hydrogen or hydroxyl groups; W represents alkylene of from 1 to about 10 carbon atoms; and B represents —NHCOR$_5$, —NHCONR$_5$R$_6$, or —NHCOOR$_5$ wherein $R_5$ and $R_6$ may be the same or different and represent hydrogen, alkyl of from 1 to about 6 carbon atoms, alkoxyalkyl wherein the alkyl groups may be the same or different and contain from 1 to about 6 carbon atoms, cycloalkyl of from 3 to about 8 carbon atoms, alkenyl of from 2 to about 6 carbon atoms, alkynyl of from 2 to about 6 carbon atoms, phenyl which may be unsubstituted or substituted with alkyl of 1 to 6 carbon atoms; furanyl, thiophenyl, imidazole, oxazole or indole, aralkyl wherein the alkyl group contains from 1 to about 6 carbon atoms and the aryl group represents phenyl unsubstituted or substituted with alkyl of from 1 to about 6 carbon atoms, or $R_5$ and $R_6$ may together with N form a pyrrolidine, piperidine, piperazine, morpholine or thiomorpholine ring and except that $R_5$ is not hydrogen when B is —NHCOOR$_5$; or a pharmaceutically acceptable salt thereof. The compounds are useful in the treatment or prophylaxis of cardiac disorders or in the treatment of glaucoma.

12 Claims, No Drawings

POLYHYDROXYBENZYLOXYPROPANOLAMINES

BACKGROUND OF THE INVENTION

Compounds of the present invention are useful because of their valuable pharmaceutical properties. They exhibit β-adrenergic blocking activity and are also useful in the treatment of glaucoma.

The present invention also relates to the treatment or prophylaxis of cardiac disorders. More particularly, the invention relates to a novel method of treatment or prophylaxis of cardiac disorders which comprises administration of β-adrenergic blocking agents and to compounds useful in such methods.

The therapeutic and prophylactic uses of compounds which block sympathetic nervous stimulation of β-adrenergic receptors in the heart, lungs, vascular system and other organs are well documented. Typically, such compounds are administered therapeutically to patients suffering from ischemic heart disease or myocardial infarction for the purpose of reducing heart work, i.e., heart rate and contractile force. Reducing heart work reduces oxygen demand, and may also actually increase oxygen supply. Thus, reducing heart work can aid in the prevention of further tissue damage and can relieve angina pectoris.

β-adrenergic stimulation may also aggravate or cause arrhythmias because of increased levels of catecholamines. Thus β-blocking agents may be employed to reduce the risks of arrhythmias.

SUMMARY OF THE INVENTION

Compounds of the present invention, are represented by the general formula

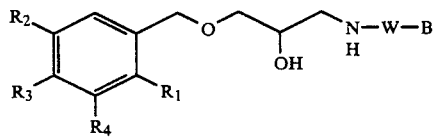

wherein $R_1$ group which may be alkyl of from 1 to about 6 carbon atoms, alkenyl of from 2 to about 6 carbon atoms, alkynyl of from 2 to about 10 carbon atoms, alkoxy wherein the alkyl group contains from 1 to about 6 carbon atoms, halogen, acetamido, amino, nitro, alkylamino of from 1 to about 6 carbon atoms, hydroxy, hydroxyalkyl of from 1 to about 6 carbon atoms, cyano or arylalkoxy wherein the alkyl group contains from 1 to about 6 carbon atoms $R_2$, $R_3$ and $R_4$ are hydrogen or hydroxyl groups or the combination of either hydrogen or hydroxyl groups; W represents alkylene of from 1 to about 10 carbon atoms; and B represents hydrogen, —NHCOR$_5$, —NHCONR$_5$R$_6$, or —NHCOOR$_5$ wherein $R_5$ and $R_6$ may be the same or different and represent hydrogen, alkyl of from 1 to about 6 carbon atoms, alkoxyalkyl wherein the alkyl groups may be the same or different and contain from 1 to about 6 carbon atoms, cycloalkyl of from 3 to about 8 carbon atoms, alkenyl of from 2 to about 6 carbon atoms, alkynyl of from 2 to about 6 carbon atoms, phenyl which may be unsubstituted or substituted with alkyl of 1 to about 6 carbon atoms; furanyl, thiophenyl, imidazole, oxazole or indole, aralkyl wherein the alkyl group contains from 1 to about 6 carbon atoms and the aryl group represents phenyl unsubstituted or substituted with alkyl of from 1 to about 6 carbon atoms, or $R_5$ and $R_6$ may together with N form a pyrrolidine, piperidine, piperazine, morpholine or thiomorpholine ring and except that $R_5$ is not hydrogen when B is —NHCOOR$_5$; or a pharmaceutically acceptable salts thereof. The compounds are useful in the treatment or prophylaxis of cardiac disorders or in the treatment of glaucoma.

DETAILED DESCRIPTION OF THE INVENTION

In accordance with the present invention, disclosed herein are compounds of the formula

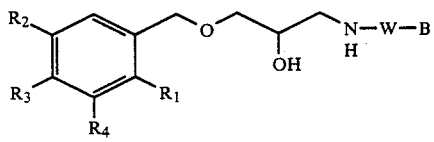

wherein $R_1$ group which may be alkyl of from 1 to about 6 carbon atoms, alkenyl of from 2 to about 6 carbon atoms, alkynyl of from 2 to about 10 carbon atoms, alkoxy wherein the alkyl group contains from 1 to about 6 carbon atoms, halogen, acetamido, amino, nitro, alkylamino of from 1 to about 6 carbon atoms, hydroxy, hydroxyalkyl of from 1 to about 6 carbon atoms, cyano or arylalkoxy wherein the alkyl group contains from 1 to about 6 carbon atoms $R_2$, $R_3$ and $R_4$ are hydrogen or hydroxyl groups or the combination of either hydrogen or hydroxyl groups; W represents alkylene of from 1 to about 10 carbon atoms; and B represents hydrogen, —NHCOR$_5$, —NHCONR$_5$R$_6$, or —NHCOOR$_5$ wherein $R_5$ and $R_6$ may be the same or different and represent hydrogen, alkyl of from 1 to about 6 carbon atoms, alkoxyalkyl wherein the alkyl groups may be the same or different and contain from 1 to about 6 carbon atoms, cycloalkyl of from 3 to about 8 carbon atoms, alkenyl of from 2 to about 6 carbon atoms, alkynyl of from 2 to about 6 carbon atoms, phenyl which may be unsubstituted or substituted with alkyl of 1 to 6 carbon atoms; furanyl, thiophenyl, imidazole, oxazole or indole, aralkyl wherein the alkyl group contains from 1 to about 6 carbon atoms and the aryl group represents phenyl unsubstituted or substituted with alkyl of from 1 to about 6 carbon atoms, or $R_5$ and $R_6$ may together with N form a pyrrolidine, piperidine, piperazine, morpholine or thiomorpholine ring and except that $R_5$ is not hydrogen when B is —NHCOOR$_5$; and the pharmaceutically acceptable salts thereof.

Some of the compounds of the present invention selectively block β-adrenergic receptors in various organs. β-receptors in the heart are generally referred to as $β_1$ receptors, and those associated with vasodilation and bronchodilation are $β_2$ receptors. Selective β-blockers are preferred for the treatment of cardiac disorders, because they may have less potential to cause hypertension or bronchoconstriction. A number of $β_1$ selective adrenergic blocking agents have been discovered [Smith, L. H., *J. Appl. Chem. Biotechnol.*, 28, 201–202 (1978)]. Most compounds are structural variations of 1-amino-3-aryloxy-2-propanol.

Compounds of the present invention are also useful for the treatment of glaucoma or lowering of intraocular pressure by topical administration of the compounds to the eye.

The present compounds may be administered to warm-blooded animals orally or parenterally. They can generally be administered with a pharmaceutical carrier. The term "pharmaceutical carrier", for the purpose of the present invention, is intended to refer to any medium that is suitable for the preparation of a dosage unit form, and, thus, includes the tablet medium or a pharmaceutically acceptable vehicle or solvent such as is ordinarily used in the preparation of intravenous or intramuscular solutions.

A pharmaceutical composition containing the compound can be administered to warm-blooded animals in parenteral or oral dosage form. For parenteral administration, amounts of from about 0.001 to about 100 mg/kg per patient, per hour, are useful, with the total dose of up to 0.2 to 2 grams per day being a suitable range for large animals, including humans. A preferred dosage range is from about 0.01 to about 10 mg/kg of body weight per hour. Suitable intravenous dosage forms are sterile solutions of the compounds of the present invention or a pharmaceutically acceptable salt thereof, containing between about 0.05% and 2% w/v of active compound. When the compounds of the invention are to be used for the treatment of cardiac disorders such as, for example, angina pectoris or cardiac arrhythmias, or for the treatment of hypertension; it is expected they would be administered at a total oral dose of about 25 mg to 1200 mg daily. Suitable oral dosage forms are tablets or capsules containing between about 25 mg to 200 mg of active compound.

For all dosage forms the above exemplified compounds can be placed in capsules, formulated into pills, wafers, or tablets in conventional fashion together with pharmaceutical carriers well known in the art. Tablets may be prepared for immediate release of the active compound or they may be made enteric, i.e., whereby the active ingredient is released slowly over a period of several hours from within the intestinal tract.

In order to illustrate the manner in which the above compounds may be prepared and the properties of the compounds, reference is made to the following examples; which, however, are not meant to limit or restrict the scope of the invention in any respect.

In the following examples, melting points were obtained on a Thomas-Hoover melting point apparatus and are uncorrected.

Scheme 1

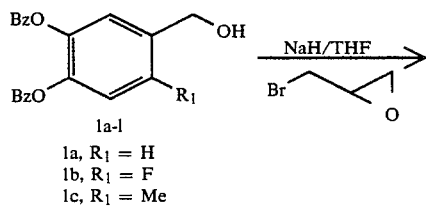

1a-1
1a, R₁ = H
1b, R₁ = F
1c, R₁ = Me

-continued
Scheme 1

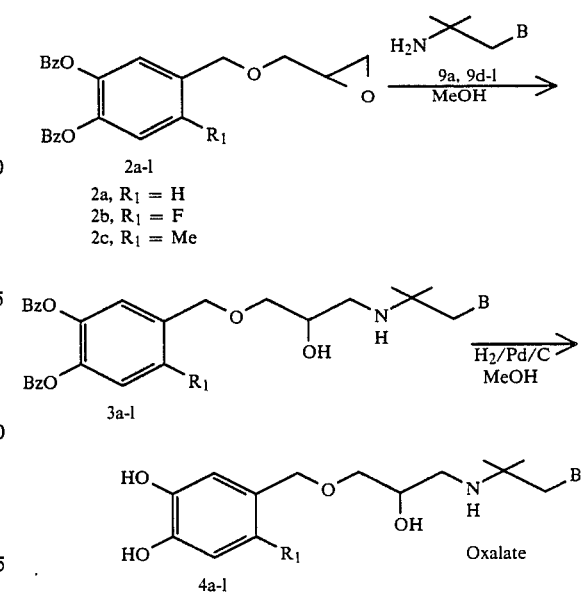

2a-1
2a, R₁ = H
2b, R₁ = F
2c, R₁ = Me 3a-1

4a-1

Preparation of 2a ($R_1$=H)

To a mixture of sodium hydride (21 g, 0.84 mole, 50% suspension in oil) in dry tetrahydrofuran (1 L) was added 3,4-dibenzyloxy benzylalcohol (1a) (135 g, 0.42 mole) with vigorous stirring. Slow evolution of hydrogen was observed. After 30 minutes, epibromohydrin (70 g, 0.5 mole) was added and stirring was continued for 16 hours. The reaction mixture was evaporated and to the resulting slurry was added ether (1 L) followed by water (very slowly) to destroy excess sodium hydride. This crude mixture was washed with brine, and evaporated under reduced pressure to give a pale yellow colored oil (150 g). This was used as it is in the next experiments.

A small portion of the above epoxide (2a) was distilled in Kugelroher apparatus at 80° C. and 5 to 50 μ to give clean colorless oil.

Elemental analysis .Cal. for $C_{24}H_{24}O_4$; Calc: C, 76.57; H, 6.43; Found: C, 76.56; H, 6.35.

Preparation of 2b, 2c and 2d

The above procedure was used to prepare 2b, 2c and 2d where 1a was replaced with 1b, 1c and 1d, respectively, A general procedure for the synthesis of 3a-1: A solution or a mixture of 2a ($R_1$=H) (20 g, 0.054 mole) and an appropriate amine 9a or 9d-1 (0.027 mole) in methanol (50 mL) was heated under reflux for 6 hours, and then evaporated under reduced pressure. The residue was extracted with ether and washed with brine, dried over MgSO₄, and then concentrated in vacuo. The resulting residue was dissolved in ethylacetate and acidified with a solution of oxalic acid in ethylacetate. In most cases, the product was crystallized immediately, and in the other cases, ether was added to induce crystallization. In those cases where no crystalline product was obtained, it was used as an oil in the next step without purification.

A general procedure for the synthesis of 4a-1: To a clear solution of 3a-1 (0.02 mole) in MeOH (in some cases warming was necessary to dissolve, if this failed, then a little TFA was added to dissolve) was added 10% Pd/C (10 mg/g of compound 3a-1) and this mixture was hydrogenated in Parr apparatus at 50 to 55 psi for 30 to 120 minutes. Filtered over celite, evaporated, redissolved in methanol (20 mL) and diluted with isopropanol (20 mL to 100 mL) and, after a few hours, crystalline solid was separated. This was recrystallized from isopropanol. M.P. are given in Table 1.

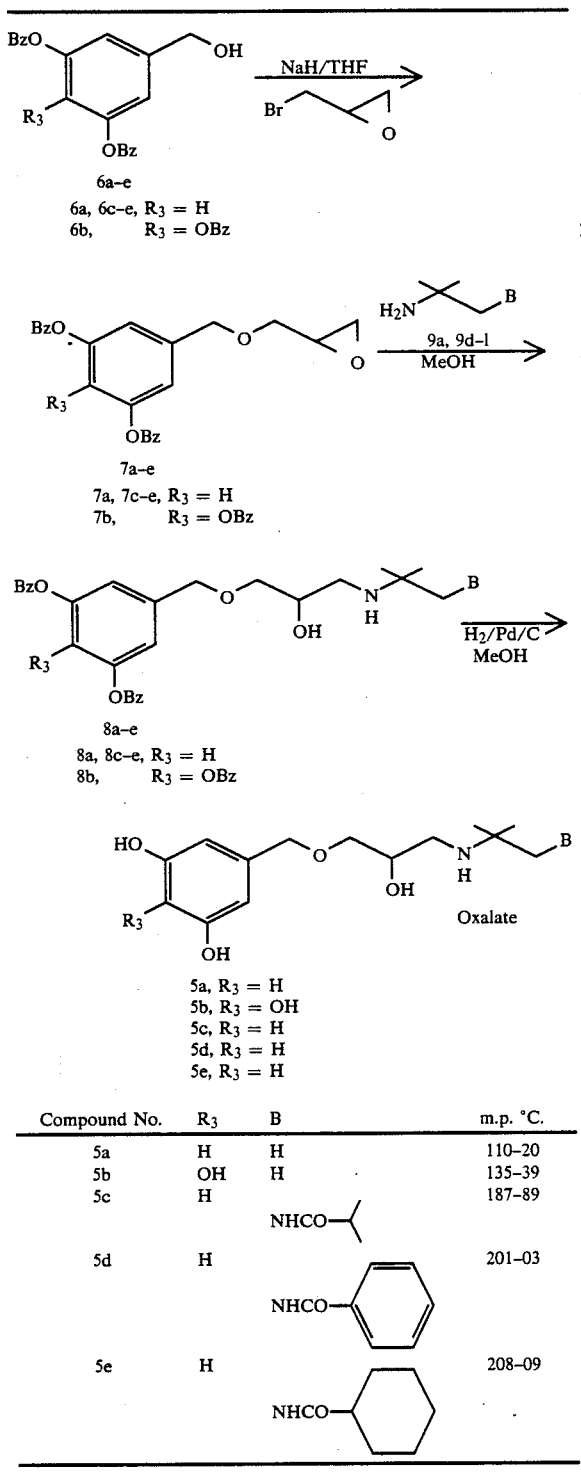

| Compound No. | $R_3$ | B | m.p. °C. |
|---|---|---|---|
| 5a | H | H | 110–20 |
| 5b | OH | H | 135–39 |
| 5c | H | NHCO—⟨ | 187–89 |
| 5d | H | NHCO—⟨phenyl⟩ | 201–03 |
| 5e | H | NHCO—⟨cyclohexyl⟩ | 208–09 |

Preparation of 5a-e

Synthesis of 5a-e from 6a-e was carried out essentially by the same method described for the preparation for 4a-1 (Scheme 1).

Preparation of 9d-1

Compound 9a was purchased from the Aldrich Chemical Company and compound 91 was synthesized by the method described in J. Med. Chem. 23, 285 (1980).

A general procedure for the preparation of 9d-91.

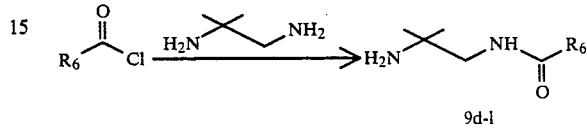

9d-1

To an ice-cooled solution of 1,2-diamino-2-methylpropane (7.9 g, 89 mmole) in toluene (50 mL) was added the appropriate acid chloride (89 mmole) and the mixture was stirred at room temperature for 16 hours. The solution was filtered and the filtrate was evaporated under reduced pressure. To this residue was added toluene (50 mL) and acetonitrile (50 mL) and concentrated in vacuo to give an oil. This oil was redissolved in toluene (50 mL) and washed with saturated sodium bicarbanate solution followed by brine, dried (MgSO$_4$), filtered and evaporated under reduced pressure, and dried under high vacuum to give appropriate oil or solid of corresponding aminoamide (9d-91).

BETA-BLOCKING ACTIVITY IN VITRO

Several of the compounds of the present invention were tested for β-blocking activity in vitro using guinea pig right atria and guinea pig tracheal strips mounted in a tissue bath containing oxygenated (95% O$_2$–5% CO$_2$) Krebs physiological salt solution at 37° C. Each tissue was suspended between a fixed glass rod and a Statham Universal Transducer connected to a Beckman recorder. Atria were allowed to beat spontaneously under a loading tension of approximately 0.5 gm. Intrinsic depressant or stimulant activity was determined for each compound by progressively increasing concentrations in the tissue baths at 60-minute intervals. Tissues were not washed between increments. The maximum concentration showing little or no cardiodepressant activity was chosen for blockade experiments. Changes in rate in response to isoproterenol, a standard β-receptor agonist, were measured in the absence and presence of test compounds. Spiral strips of guinea pig trachea were suspended under 5 gm resting tension and incubated with phentolamine, tropolone and cocaine. Active tension was generated by addition of carbachol (3.0×10$^{-7}$M) and decreases in tension in response to isoproterenol were quantitated. Cumulative concentration-response curves were produced with isoproterenol both before and after 60-minute incubation of test compounds with atria and trachea. Compounds with β-blocking activity shifted concentration-response curves to the right. The blocking potency of test compounds was estimated by computing pA$_2$ values ($-\log$ K$_8$) by the method of Furchgott, the Pharmacological Differentiation of Adrenergic Receptors, *Ann. N.Y. Acad. Sci.*, 139:553–570 (1967). Comparison of blockade of right atrial and tracheal responses to isoproterenol permits assessment of cardioselectivity of test compounds; i.e., cardioselective compounds are relatively more effective in blocking atrial rate than tracheal force response to isoproterenol. The degree of cardioselectivity was estimated from the ratio, $K\beta$ trachea/$K\beta$ atria ($10^{(pA_2 atria - pA_2 trachea)}$). A ratio greater than one indicates cardioselectivity. Test drugs were dissolved in distilled water and added to the bath (30 mL) in a volume of 10 or 100 μL. The results of the in vitro tests are contained in Table 1. All of the test compounds are active β-blockers.

DURATION AND POTENCY OF BETA-BLOCKING ACTION IN VIVO

The duration of β-blockage was determined in vivo using pentobarbital-anesthetized dogs instrumented for measurement of heart rate using a Beckman cardiotachometer triggered electronically by a phasic aortic blood pressure signal. Both vagus nerves were severed in the cervical region and the animals were mechanically ventilated. The experimental design used employed a 3-hour infusion of test compound. Bolus doses of isoproterenol (0.5 μg/kg) were used to assess the degree of β-blockage and recovery from β-blockage after determination of the infusion. The doses were spaced at 10-minute intervals and were given before, during and following the infusion of test compounds. The infusion rate was adjusted so that at the end of the 3-hour infusion period the degree of isoproterenol inhibition averaged about 50% of control. Following termination of blocker infusion, percent recovery from β-blockade was computed and the time associated with 80% recovery estimated. The results are contained in Table 1.

TABLE 1

| No. | pA2 Atria | Potency mcg/k/m | % I | 50% min. | 80% min. |
|---|---|---|---|---|---|
| 4a | 6.5 | 112 | 45 | 5 | 16 |
| 4b | 7.0 | | | | |
| 4c | 6.0 | | | | |
| 4d | 6.6 | | | | |
| 4e | 6.6 | 36 | 35 | 11 | 39 |
| 4f | 6.8 | | | | |
| 4g | 6.8 | 1.7 | 64 | 46 | >60 |
| 4h | 7.5 | | | | |
| 4i | 6.6 | 12.3 | 45 | 8 | 31 |
| 4j | 6.6 | 11 | 42 | 3 | 17 |
| 4k | 6.5 | 1.3 | 69 | 53 | >60 |
| 4l | 6.0 | | | | |
| 5a | 6.5 | | | | |
| 5b | 6.0 | | | | |
| 5c | 7.1 | | | | |
| 5d | 7.1 | | | | |
| 5e | 6.7 | | | | |

What is claimed is:

1. A compound of the formula

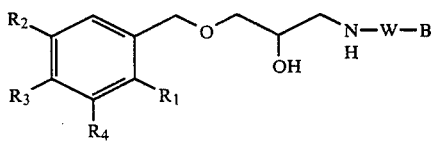

wherein $R_1$ may be alkyl of from 1 to about 6 carbon atoms, alkenyl of from 2 to about 6 carbon atoms, alkynyl of from 2 to about 10 carbon atoms, cycloalkyl of from 3 to about 8 carbon atoms, halo, acetamido, amino, nitro, alkylamino of from 1 to about 6 carbon atoms, hydroxy, hydroxyalkyl of from 1 to about 6 carbon atoms, or cyano, $R_2$, $R_3$ and $R_4$ are hydrogen or hydroxyl or the combination of either hydrogen or hydroxyl; W represents alkylene of from 1 to about 10 carbon atoms; and B represents hydrogen; or a pharmaceutically acceptable salt thereof.

2. A compound of claim 1 wherein $R_1$ may be hydrogen, alkyl of from 1 to about 6 carbon atoms, or halo, $R_2$, $R_3$ and $R_4$ represent hydrogen or hydroxy or the combination of either hydrogen or hydroxy, W is 1,1-dimethylethylene, and B is hydrogen.

3. A compound of claim 2 wherein $R_1$ is hydrogen, alkyl of from 1 to about 6 carbon atoms, $R_2$, $R_3$ and $R_4$ are hydrogen or hydroxy or the combination of hydrogen or hydroxy, W is 1,1-dimethylethylene, and B is hydrogen.

4. A compound of claim 3 wherein $R_1$ is fluoro, $R_2$ is hydrogen, $R_3$ and $R_4$ are each hydroxy, W is 1,1-dimethylethylene and B is hydrogen.

5. A method of treating cardiac disorders in a patient comprising administering to a patient in need of such treatment a therapeutically effective amount of a compound of the formula

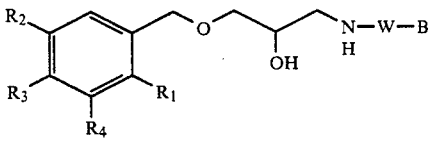

wherein $R_1$ may be alkyl of from 1 to about 6 carbon atoms, alkenyl of from 2 to about 6 carbon atoms, alkynyl of from 2 to about 10 carbon atoms, cycloalkyl of from 3 to about 8 carbon atoms, halo, acetamido, amino, nitro, alkylamino of from 1 to about 6 carbon atoms, hydroxy, hydroxyalkyl of from 1 to about 6 carbon atoms, or cyano, $R_2$, $R_3$ and $R_4$ are hydrogen or hydroxyl or the combination of either hydrogen or hydroxyl; W represents alkylene of from 1 to about 10 carbon atoms; and B represents hydrogen; or a pharmaceutically acceptable salt thereof.

6. The method of claim 5 wherein $R_1$ may be hydrogen, alkyl of from 1 to about 6 carbon atoms, or halo, $R_2$, $R_3$ and $R_4$ represent hydrogen or hydroxy or the combination of either hydrogen or hydroxy, W is 1,1-dimethylethylene, and B is hydrogen.

7. The method of claim 6 wherein $R_1$ is hydrogen, alkyl of from 1 to about 6 carbon atoms, $R_2$, $R_3$ and $R_4$ are hydrogen or hydroxy or the combination of hydrogen or hydroxy, W is 1,1-dimethylethylene, and B is hydrogen.

8. The method of claim 7 wherein $R_1$ is fluoro, $R_2$ is hydrogen, $R_3$ and $R_4$ are each hydroxy, W is 1,1-dimethylethylene and B is hydrogen.

9. A pharmaceutical composition for treating cardiac conditions which composition contains an effective amount for treating such conditions of a compound having beta-adrenergic activity of the formula

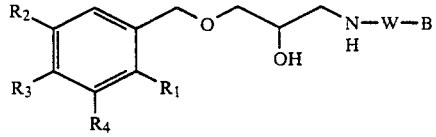

wherein $R_1$ may be alkyl of from 1 to about 6 carbon atoms, alkenyl of from 2 to about 6 carbon atoms, alkynyl of from 2 to about 10 carbon atoms, cycloalkyl of from 3 to about 8 carbon atoms, halo, acetamido, amino, nitro, alkylamino of from 1 to about 6 carbon atoms, hydroxy, hydroxyalkyl of from 1 to about 6 carbon atoms, or cyano, $R_2$, $R_3$ and $R_4$ are hydrogen or hydroxyl or the combination of either hydrogen or hydroxyl; W represents alkylene of from 1 to about 10 carbon atoms; and B represents hydrogen; or a pharmaceutically acceptable salt thereof, in admixture with a pharmaceutically acceptable carrier or diluent.

10. The composition of claim 9 wherein $R_1$ may be hydrogen, alkyl of from 1 to about 6 carbon atoms, or halo, $R_2$, $R_3$ and $R_4$ represent hydrogen or hydroxy or the combination of either hydrogen or hydroxy, W is 1,1-dimethylethylene, and B is hydrogen.

11. The composition of claim 10 wherein $R_1$ is hydrogen, alkyl of from 1 to about 6 carbon atoms, $R_2$, $R_3$ and $R_4$ are hydrogen or hydroxy or the combination of hydrogen or hydroxy, W is 1,1-dimethylethylene, and B is hydrogen.

12. The composition of claim 11 wherein $R_1$ is fluoro, $R_2$ is hydrogen, $R_3$ and $R_4$ are each hydroxy, W is 1,1-dimethylethylene and B is hydrogen.

* * * * *